United States Patent [19]
Burdet et al.

[11] Patent Number: 5,786,518
[45] Date of Patent: Jul. 28, 1998

[54] PROCESS FOR THE MANUFACTURE OF A GAMMA-HALOTIGLIC ALDEHYDE

[75] Inventors: Bruno Burdet, Baldersheim, France; Paul Nösberger, Birsfelden; August Rüttimann, Arlesheim, both of Switzerland

[73] Assignee: Roche Vitamins Inc., Parsippany, N.J.

[21] Appl. No.: 904,523

[22] Filed: Aug. 1, 1997

[30] Foreign Application Priority Data

Aug. 19, 1996 [EP] European Pat. Off. .............. 96113248

[51] Int. Cl.$^6$ ...................................................... C07C 45/00
[52] U.S. Cl. ............................ 568/487; 568/486; 568/488
[58] Field of Search .................................... 568/486, 487, 568/488

[56] References Cited

U.S. PATENT DOCUMENTS 2,165,962  10/1939  Mueller-Cunradl et al. .
4,288,635   9/1981  Gray .

OTHER PUBLICATIONS

Eletti–Bianchi et al., "A Two–Step Synthesis of (E)–4–Chloro–2–methylcrotonaldehyde from Isoprene ...", J. Org. Chem. 41:1648–1650 (1976).

Nederlof et al., "An Effective [1,4]–Charge Affinity Invesion of Sulfur Functionalized Isoprenes, Tetrahedron Letters, 34:2205–2207 (1978).

Dietl et al., Coper (II)—Catalyzed γ–Chlorination of α, β–Unsaturated Aldehydes and Ketones, Tetrahedron Letters No. 20:1719–1720 (1973).

Makin et al, "The Chemistry of Unsaturated Ethers", J. Gen. Chem. USSR 32;1088–1092 (1962).

S. M. Makin, "The Enol Ether Synthesis of Polyenes", Pure & Appl. Chem. 47:173–181 (1976).

S.M. Makin, "Chemistry of Unsaturated Ethers", Chem. USSR 32:3105–3106 (1961).

A. F. Thomas, "Addition of a Functionalized Iosoprenme Unit to an Allyl Alcohol", J.A.C.S. 91:3281–3289 (1969).

Hoaglin et al., "Reaction of Acetals and α,β–Unsaturated Ethers, J.A.C.S 71:3468–3472 (1949).

Fischer et al., "$C_5$ Building Blocks of Terpene Syntheses: γ–Acetoxylation of (E)–2–Methyl–2–butenals, Angew. Chem. Int. Ed. Engl. 27, No. 2, pp. 285–297 (1988).

*Primary Examiner*—Alan Siegel
*Attorney, Agent, or Firm*—George W. Johnston; Dennis P. Tramaloni; Bruce A. Pokras

[57] ABSTRACT

A novel process for the manufacture of a γ-halotiglic aldehyde $HalH_2C-CH=C(CH_3)-CHO$ [I], wherein Hal signifies chlorine or bromine, comprises haloalkoxylating a 1-alkoxy-2-methyl-1,3-butadiene $H_2C=CH-C(CH_3)=CH-OR^1$ [II], wherein $R^1$ signifies $C_{1-4}$-alkyl, using a particular halogenating agent in a $C_{1-4}$-alkanol ($R^2OH$) and hydrolyzing the thus-obtained γ-halotiglic aldehyde dialkyl acetal $HalH_2C-CH=C(CH_3)-CH(OR^1)(OR^2)$ [III] to the desired γ-chloro- or γ-bromotiglic aldehyde I. The halogenating agent used in this process is selected from an alkali metal hypochlorite, an alkali metal hypobromite, an alkaline earth metal hypochlorite, an alkaline earth metal hypobromite, tert.butyl hypochlorite, N-bromoacetamide, 1,3-dichloro-5,5-dimethylhydantoin and 1,3-dibromo-5,5-dimethylhydantoin. Further aspects of the present invention are the use of the thus-manufactured γ-halotiglic aldehyde for the production of γ-acetoxy-tiglic aldehyde or of a Wittig aldehyde halide $Hal-Ph_3P^+CH_2-CH=C(CH_3)-CHO$ [VII], wherein Hal signifies chlorine or bromine and Ph signifies phenyl, as well as a process for the catalytic dealkoxylation of the 1,1,3-trialkoxy-2-methyl-butane $CH_3-CH(OR^1)-CH(CH_3)-CH(OR^1)_2$ [VI] to the corresponding 1-alkoxy-2-methyl-1,3-butadiene II in the gas phase using an aluminium silicate of medium specific surface as the catalyst. The products I, γ-acetoxy-tiglic aldehyde and VII are known, important intermediates for the production of various apocarotenoids and diapocarotenoids as well as of Vitamin A.

8 Claims, No Drawings

PROCESS FOR THE MANUFACTURE OF A GAMMA-HALOTIGLIC ALDEHYDE

BACKGROUND OF THE INVENTION

The present invention is concerned with a novel process for the manufacture of a γ-halotiglic aldehyde and with the use of the thus-manufactured γ-halotiglic aldehyde for the production of γ-acetoxy-tiglic aldehyde or of certain $C_5$-Wittig aldehyde halides. These products are known, important intermediates for the manufacture of various apocarotenals and diapocarotenals as well as of vitamin A.

γ-Chlorotiglic aldehyde and the corresponding γ-bromo compound are known and can be manufactured according to a number of known methods starting from methylglyoxal dimethyl acetal [see Belgian Patent 633,007, German Offenlegungsschriften (DOS) 1,188,577 and 1,952,649 as well as Finn. Chem. Lett. 1984, 102 et seq.], from isoprene [DOS 2,620,968, U.S. Pat. No. 4,288,635, J. Org. Chem. 41, 1648 et seq. (1976), Rec. Trav. Chim. Pays-Bas 99, 384 et seq. (1980) as well as Tetrahedron 34, 2205 et seq. (1978)], from 3-methyl-2-butenyl chloride [Nippon Kagaku Kaishi 1975, 2246 et seq./Chem. Abs. 84(9), 58575s], from tiglic aldehyde [Tetr. Lett. 20, 1719 et seq. (1973)] or from 1-methoxy/ethoxy-2-methyl-1,3-butadiene [J. Gen. Chem. USSR 32, 1088 et seq. (1962; English translation), Russian Chem. Rev. 38, 237 et seq. (1969), Pure & Appl. Chem. 47, 173 et seq. (1976), J. Gen. Chem. USSR 32, 3105 et seq. (1961; English translation) as well as Helv. Chim Acta 54, 1369 et seq. (1971)]. With respect to the last-mentioned method, the 1-alkoxy-2-methyl-1,3-butadiene can be bromoalkoxylated using N-bromosuccinimide in methanol or ethanol to give the corresponding γ-bromotiglic aldehyde dialkyl acetal, from which in turn there can be produced as required the corresponding γ-acetoxy-tiglic aldehyde acetal and subsequently γ-acetoxy-tiglic aldehyde or γ-bromotiglic aldehyde. From the respective scientific literature it is not evident that brominating agents other than N-bromosuccinimide have been used for the manufacture of γ-bromotiglic aldehyde from the 1-alkoxy-2-methyl-1,3-butadiene. Further, the manufacture of γ-chlorotiglic aldehyde starting from this 1,3-butadiene derivative by haloalkoxylation is also not known from the scientific literature. However, it can be expected that the corresponding N-chloro compound, i.e. N-chlorosuccinimide, could be used instead of N-bromosuccinimide for this purpose and in an analogous manner.

SUMMARY OF THE INVENTION

It has now been found that a 1-alkoxy-2-methyl-1,3-butadiene can also be haloalkoxylated directly using a halogenating agent hitherto never used for this purpose and an alcohol to form the respective γ-halotiglic aldehyde dialkyl acetal and, after subsequent hydrolysis of this acetal, the γ-halotiglic aldehyde can be obtained. The halogenating agent is an alkali metal or alkaline earth metal hypochlorite or hypobromite, tert.-butyl hypochlorite, N-bromoacetamide or 1,3-dichloro- or 1,3-dibromo-5,5-dimethyl-hydantoin. These halogenating agents are known compounds and for the most part are readily available commercially. Thus, for example, the aqueous, so-called "Javelle water" (potassium hypochlorite) or Eau de Labarraque (sodium hypochlorite) are both readily available commercially and are cheap, so that their direct use represents a considerable improvement over the halogenating agents previously used for this purpose, primarily N-bromosuccinimide. The known use of N-bromosuccinimide gives succinimide as a byproduct of the reaction, which must be regenerated in a plant scale production procedure.

The 1-alkoxy-2-methyl-1,3-butadienes used as the substrate in the process in accordance with the invention are readily accessible from cheap starting materials, as will be explained in more detail hereinafter.

DETAILED DESCRIPTION IF THE INVENTION

The present invention is directed to a process for making a γ-chloro- or γ-bromotiglic aldehyde of the formula:

$$HalH_2C-CH=C(CH_3)-CHO \qquad I$$

wherein Hal is chlorine or bromine, which process comprises:

1) haloalkoxylating a 1-alkoxy-2-methyl-1,3-butadiene of the formula:

$$H_2C=CH-C(CH_3)=CH-OR^1 \qquad II$$

wherein $R^1$ is $C_{1-4}$-alkyl,
by reacting the 1-alkoxy-2-methyl-1,3-butadiene with a halogenating agent and an alcohol of the formula $R^2OH$, wherein the halogenating agent is selected from the group consisting of an alkali metal hypochlorite, an alkali metal hypobromite, an alkaline earth metal hypochlorite, an alkaline earth metal hypobromite, tert.butyl hypochlorite, N-bromoacetamide, 1,3-dichloro-5,5-dimethyl-hydantoin and 1,3-dibromo-5,5-dimethyl-hydantoin, and $R^2$ is $C_{1-4}$-alkyl, to obtain a γ-halotiglic aldehyde dialkyl acetal of the formula:

$$HalH_2C-CH=C(CH_3)-CH(OR^1)(OR^2) \qquad III$$

wherein Hal, $R^1$ and $R^2$ are as above, and 2) hydrolyzing the γ-halotiglic aldehyde dialkyl acetal to produce the γ-chloro- or γ-bromotiglic aldehyde.

In the above definition of the process in accordance with the invention there are to be understood under the term "$C_{1-4}$-alkyl" not only straight-chain alkyl groups but also $C_{3-4}$ branched alkyl groups. However, $R^1$ and $R^2$ are preferably methyl or ethyl.

The alkali metal or alkaline earth metal hypochlorite or hypobromite (hereinafter denoted in a generalized form as "metal hypohalite") usable in the first step of the process is preferably sodium or potassium hypochlorite, sodium or potassium hypobromite, calcium hypochlorite or calcium hypobromite. Sodium or potassium hypochlorite is preferably used as the chlorinating agent, and sodium or potassium hypobromite is preferably used as the brominating agent.

When the alkali metal hypohalites are used, the haloalkoxylation comprising the first step of the process of the invention is conveniently effected using an aqueous solution of the alkali metal hypohalite, with the water-miscible alcohol $R^2OH$ also being necessarily present in the reaction mixture. For example a "Javelle water", which has a concentration of about 13% w/w (weight percent) of potassium hypochlorite and which is readily available commercially, is an especially suitable aqueous potassium hypochlorite solution. Aqueous potassium hypochlorite solutions having concentrations lower or higher than 13% w/w can, however, also be used effectively, and this also applies to the corresponding aqueous sodium hypochlorite, sodium hypobromite or potassium hypobromite solution. An aqueous solution of the alkali metal hypochlorite or hypobromite having a concentration between about 5% w/w and about 30% w/w is preferably used. The alkali metal hypohalite concentration is especially preferred to be from about 10% w/w and about 20% w/w.

When a halogenating agent other than an alkali metal hypohalite is employed, it is conveniently used as such, i.e., not in an aqueous solution. Tert.butyl hypochlorite is a liquid; calcium hypochlorite, N-bromoacetamide, 1,3-dichloro-5,5-dimethyl-hydantoin and 1,3-dibromo-5,5-dimethylhydantoin are on the other hand solid at normal pressure and room temperature.

The ratio of the halogenating agent, the alcohol $R^2OH$ and the compound of formula II is not critical, so long as some of the compound of formula III is formed. Preferably, the halogenating agent is used in the process of the invention in an amount from about 1.1 to about 1.4 equivalents of the halogenating agent per equivalent of 1-alkoxy-2-methyl-1,3-butadiene of formula II. The alcohol $R^2OH$ is generally used as a solvent for the haloalkoxylation reaction, and so is used in a large excess, preferably in a ten to thirty fold excess. The temperature at which the haloalkoxylation is carried out is not critical. The haloalkoxylation is preferably effected in a temperature range from about −20° C. to room temperature, especially at temperatures from about −10° C. and about +5° C. In this manner the haloalkoxylation is normally completed in a reaction time of up to about three hours.

In the particular case when sodium hypobromite is used as the brominating agent, this is advantageously freshly prepared prior to the haloalkoxylation by any conventional means, preferably by the dropwise addition of bromine to aqueous sodium hydroxide solution at about 0° C. About equimolar amounts of bromine and sodium hydroxide (as such) are preferably used.

The hydrolysis of the γ-halotiglic aldehyde dialkyl acetal of formula III to the desired γ-chloro- or γ-bromotiglic aldehyde of formula I, which follows the haloalkoxylation and which represents the second step of the process, can be carried out by any conventional means. The hydrolysis may be performed after isolating the acetal from the reaction mixture by conventional means. However, it has been found to be more convenient not to undertake such an isolation and subsequent hydrolysis, but immediately after obtaining a solution of the acetal in an organic solvent during the working-up of the haloalkoxylation reaction mixture to hydrolyze the acetal in this solution. The working-up and subsequent hydrolysis can be conveniently carried out by conventional means, for example, by combining the mixture obtained after completion of the haloalkoxylation with water, preferably by pouring the mixture into water, extracting the resulting aqueous mixture (generally for the most part an aqueous solution) with a suitable organic solvent and treating the thus-obtained solution of the acetal in the organic solvent with an aqueous mineral acid to hydrolyze the acetal and produce the desired γ-halotiglic aldehyde. Any conventional water-immiscible organic solvent in which the acetal is soluble and in which the acetal can by hydrolyzed may be used for the extraction. An aliphatic, alicyclic or aromatic hydrocarbon, e.g., n-pentane or n-hexane, cyclohexane or toluene; a halogenated aliphatic hydrocarbon, e.g., methylene chloride or chloroform; an aliphatic ether, e.g., diethyl ether or tert.butyl methyl ether; or an aliphatic ester, e.g., ethyl acetate, is an especially suitable solvent for the extraction.

If desired, the separated extraction solution can be washed, preferably with water, prior to its treatment with acid. Any conventional acid capable of hydrolyzing the acetal to the desired γ-halotiglic aldehyde may be used. Preferably, a mineral acid such as sulphuric acid or hydrochloric acid is used, its concentration suitably being in the range of about 0.5% w/w to about 20% w/w and the treatment preferably being effected in the temperature range of about 0° C. to room temperature while stirring. The acid treatment takes, for example, about 30 minutes to about 2 hours.

The thus-manufactured γ-chloro- or γ-bromotiglic aldehyde of formula I can be isolated from the reaction mixture in a manner known per se and, if desired, purified. Typically, the aqueous phase is separated and the organic phase containing the desired γ-chloro- or γ-tiglic aldehyde is washed with water and/or aqueous sodium chloride solution and/or sodium bicarbonate solution, dried and concentrated. The thus-isolated crude product, which has been washed at least to some extent, can then, if desired, be purified further, for example by column chromatography, e.g., using silica gel as the stationary phase and eluting agents such as cyclohexane, ethyl acetate or mixtures thereof. Both γ-chloro- and γ-bromotiglic aldehyde are liquids at normal pressure and room temperature. As an alternative to the isolation and optional purification, the hydrolysis product of formula I can be converted directly in a further reaction step into, e.g., γ-acetoxy-tiglic aldehyde or a corresponding Wittig aldehyde chloride or bromide, using a "through process". In this, the crude product of the hydrolysis is converted directly in the subsequent reaction without separating the organic solvent used in the working-up of the hydrolysis, since the respective solvent can also be used in the further process step.

Some of the 1-alkoxy-2-methyl-1,3-butadienes of formula II which are used as starting materials in the process in accordance with the invention are known compounds; the remainder can be produced from known starting materials according to methods known per se.

Thus, for example, 1-ethoxy-2-methyl-1,3-butadiene (formula II, wherein $R^1$ signifies ethyl) has been known from the literature for a long time [see, inter alia, J.A.C.S. 91, 3281 et seq. (1969), Bull. Soc. Chim. Fr. 1963, 1646 et seq., as well as J. Gen. Chem. USSR 29, 3649 et seq. (1959)] and has been produced in each case by the two-fold cleavage of ethanol from 1,1,3-triethoxy-2-methyl-butane. The butane derivative, in turn, can be produced by a known enol ether condensation (see U.S. Pat. No. 2,165,962) from the two readily accessible starting materials, acetaldehyde diethyl acetal and ethyl (1-propenyl) ether [see, furthermore, J.A.C.S. 71, 3468 et seq. (1949) as well as J. Gen. Chem. USSR 29, 3641 et seq. (1959)]. This reaction involves heating about 2 to 3 equivalents of the acetal per equivalent of ethyl propenyl ether at about 35° C. for up to about 2 hours in the presence of about 0.2 mol percent of boron trifluoride etherate as the catalyst in the absence of a solvent, the desired butane derivative being obtained in about 66% yield. The subsequent two-fold cleavage of ethanol from the 1,1,3-triethoxy-2-methyl-butane can be realised in two different ways according to the pertinent state of the art:

(i) by cleavage in the liquid phase by the dropwise addition of the 1,1,3-triethoxy-2-methyl-butane to isoquinoline containing a catalytic amount of p-toluenesulphonic acid at about 220° C. and distilling off the 1-ethoxy-2-methyl-1,3-butadiene which is thereby formed. The yields in this method, described in Bull. Soc. Chim. Fr. 1963, 1646 et seq., are however mediocre (about 40–50%); or (ii) by cleavage in the gas phase at 300°–350° C. under a vacuum on an acid catalyst, e.g., monosodium phosphate [J. Gen. Chem. USSR 29, 3649 et seq. (1959)].

1-Methoxy-2-methyl-1,3-butadiene (formula II, wherein $R^1$ signifies methyl) is also known from the literature

[Japanese Patent Publication (Kokai) 50891/1989]. It can be produced, for example, analogously to the above described production of 1-ethoxy-2-methyl-1,3-butadiene starting from acetaldehyde dimethyl acetal and methyl (1-propenyl) ether via 1,1,3-trimethoxy-2-methyl-butane.

The remaining 1-alkoxy-2-methyl-1,3-butadienes of formula II are in part known compounds and can be produced analogously to the aforementioned compounds. The following Reaction Scheme is a compilation of the multi-step procedure explained in more detail above in accordance with which all 1-alkoxy-2-methyl-1,3-butadienes of formula II can be produced:

Reaction Scheme

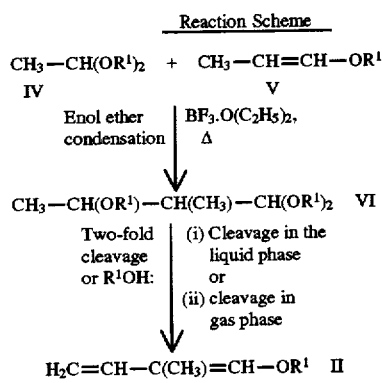

$R^1$ in this Reaction Scheme has the significance given above. The intermediate of formula VI and the product of formula II can be isolated and purified in a manner known per se.

A review of the production of 1-alkoxy-2-methyl-1,3-butadienes appears in Russian Chem. Rev. 38, 237 et seq. (1969) and in Pure & Appl. Chem. 47, 173 et seq. (1976); for additional literature concerning the production by gas phase catalysis reference is made to Lieb. Ann. Chem. 568, 1 et seq. (1950), Can. J. Res. B 28, 689 et seq. (1950), ibid. B 25, 118 et seq. (1947) as well as Chem. Ber. 77, 108 et seq. (1944).

The cleavage of the alcohol $R^1OH$ (dealkoxylation) from the trialkoxybutanes of formula VI in the gas phase [method (ii)] at elevated temperature on a fixed, solid catalyst ("solid bed catalyst") is much more attractive for an industrial process than a cleavage in the liquid phase [method (i)], since method (ii) requires, inter alia, no solvent and involves a simple reaction procedure and working-up. Accordingly, it is preferred to carry out the dealkoxylation in the gas phase. In general, catalysts can be used which are similar to catalysts used for the dealkoxylation of unsubstituted acetals. Moreover, such a dealkoxylation is conveniently carried out at temperatures between about 300° C. and about 350° C.

In investigations with respect to the dealkoxylation there has now been found an especially well suited type of catalyst which has hitherto never been used for this purpose. This catalyst is a weakly acidic aluminium silicate. As is known, aluminium silicates exist as a mixture of aluminium oxide ($Al_2O_3$) and silica ($SiO_2$), in which the ($Al_2O_3$):($SiO_2$) ratio can vary over a wide range. The aluminium silicate catalyst, which is very well suited for the catalytic dealkoxylation described herein, conveniently has a medium specific surface, preferably in a range of about 5 to about 50 m$^2$/g. Furthermore, the aluminium oxide content of the aluminium silicate catalyst is preferably in the α-form.

The present invention accordingly also includes as a further aspect a process for the catalytic dealkoxylation of a 1,1,3-trialkoxy-2-methyl-butane of the formula:

$$CH_3CH(OR^1)\text{—}CH(CH_3)\text{—}CH(OR^1)_2 \quad VI$$

wherein $R^1$ is $C_{1-4}$-alkyl, to produce a 1-alkoxy-2-methyl-1,3-butadiene of the formula:

$$H_2C=CH\text{—}C(CH_3)=CH\text{—}OR^1 \quad II$$

which process comprises contacting the 1,1,3-trialkoxy-2-methyl-butane in the gas phase with an aluminium silicate catalyst having a surface area in the range from about 5 to about 50 m$^2$/g for a sufficient time and at a sufficient temperature to dealkoxylate the 1,1,3-trialkoxy-2-methyl-butane whereby the 1-alkoxy-2-methyl-1,3-butadiene is produced.

A cleavage selectivity of about 90% with a conversion of about 90% can be achieved using such a catalyst, preferably one having a specific surface in the range of about 5 to about 50 m$^2$/g and, furthermore, one in which the aluminium oxide content is present in the α-form.

The above process is conveniently carried out analogously to known dealkoxylations in the gas phase, the characterizing feature of the dealkoxylation in accordance with the invention being the use of the aluminium silicate catalyst. Preferably, reaction temperatures in the range of about 250° C. to about 400° C., more preferably temperatures of about 300° C. to about 350° C., and pressures of about 1 kPa to about 200 kPa are used. The dealkoxylation is preferably carried out at atmospheric pressure.

Preferably, the dealkoxylation is effected in a solid bed reactor, with the 1,1,3-trialkoxy-2-methyl-butane educt, optionally diluted with an inert gas, being conducted continuously over the aluminium silicate catalyst as the solid bed in a reaction column and the resulting corresponding 1-alkoxy-2-methyl-1,3-butadiene being removed at the end or the reaction column. The methodology is known per se, and this also applies to the requisite apparatus. Nitrogen or carbon dioxide, for example, can be used as the inert gas. The residence time on the catalyst bed is preferably in the range of about 0.1 to about 10 seconds, more preferably in the range of about 0.5 to about 5 seconds. The conversion of the educt can be optimised by adjusting the reaction temperature, residence time and other reaction parameters in order to achieve a yield of product which is as high as possible and to insure that as few byproducts as possible are formed.

As mentioned earlier, the γ-chloro- or γ-bromotiglic aldehyde of formula I manufactured in accordance with the invention can be used for the production of various additional intermediates which, in turn, are finally of use for the manufacture of apocarotenals and diapocarotenals, as well as vitamin A.

Thus, γ-halotiglic aldehyde can be used, for example, for the production of γ-acetoxy-tiglic aldehyde, an important building block for the manufacture of vitamin A [see Angew. Chem. 72, 811 et seq. (1960)]. It can be manufactured starting from γ-halotiglic aldehyde in many ways [see, inter alia, Angew. Chem. 100, 301 et seq. (1988), DOS 1,227,000, 2,844,949, 2,943,407 and 3,639,562, Bull. Soc. Chim. France 1955, 209 et seq., J. Gen. Chem. USSR 32, 1088 et seq. (1962; English translation), Russian Chem. Rev. 38, 237 et seq. (1969) and Pure & Appl. Chem. 47, 173 et seq. (1976)].

An attractive route from the γ-halotiglic aldehyde to γ-acetoxy-tiglic aldehyde involves reacting the former tiglic aldehyde derivative or an acetal thereof, especially one of formula III, with sodium acetate or potassium acetate. Thus, 1,1-diethoxy-4-acetoxy-2-methyl-2-butene has been obtained in about 78% yield by weight (without, however, purification data) according to J. Gen. Chem. USSR 32, 1088 et seq. (1962) by reacting γ-bromotiglic aldehyde diethyl acetal with potassium acetate in refluxing ethanol. It is also known from DOS 1,227,000 that the γ-halotiglic aldehyde can be converted in good yield (84–86%) into γ-acetoxy-tiglic aldehyde with sodium acetate or potassium acetate in water at about 100° C.

In addition to these known methods it has now been found that the substitution with sodium acetate or potassium acetate can also be carried out very readily in the absence of water and with high yield in an organic solvent, e.g. toluene, and in the presence of a phase transfer catalyst, e.g. tetraethylammonium bromide. The performance of this substitution under anhydrous conditions is in strong contrast to the teaching of DOS 1,227,000 disclosed that no satisfactory substitution yields could be achieved in the reaction of γ-chloro- or γ-bromotiglic aldehyde with metal salts of carboxylic acids, e.g., with potassium acetate, under anhydrous conditions. The novel variant permits a simple working-up of the reaction mixture and isolation of the γ-acetoxy-tiglic aldehyde, in the latter case by removal of the alkali halide which is formed and the excess alkali acetate by filtration, followed by a distillation of the product. When potassium acetate is used as the reagent, the reaction is preferably effected at about 80° C., and when the somewhat less reactive sodium acetate is used, preferably at about 110° C. As expected, the γ-chlorotiglic aldehyde is also less reactive than the corresponding bromoaldehyde.

The novel process variant can, moreover, be effected as a continuation of a "through process", starting from a 1-alkoxy-2-methyl-1,3-butadiene of formula II via a γ-halotiglic aldehyde dialkyl acetal of formula III and the corresponding γ-halotiglic aldehyde of formula I, i.e., as a subsequent step of the above defined process in accordance with the invention.

The use of the γ-chloro- or γ-bromotiglic aldehyde of formula I manufactured in accordance with the invention for the production of γ-acetoxytiglic aldehyde forms a further aspect of the present invention.

As an alternative to the conversion of the γ-chloro- or γ-bromotiglic aldehyde manufactured in accordance with the invention into γ-acetoxy-tiglic aldehyde, the γ-halotiglic aldehyde can be converted by reaction with triphenylphosphine into the corresponding, known C₅-Wittig aldehyde halide (hereinafter "Wittig aldehyde salt") of the formula:

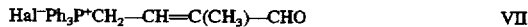

Hal⁻Ph₃P⁺CH₂—CH=C(CH₃)—CHO     VII wherein Hal is chlorine or bromine and Ph is phenyl. This Wittig aldehyde salt or its protected, especially acetalized, form is, as is known, an important building block for the manufacture of various apocarotenals, e.g. β-apo-8'-carotenal (see DOS 1,210,780) and diapocarotenals, e.g., crocetin dialdehyde (see Finn. Chem. Lett. 1984, 102 et seq.). It can be produced readily in accordance with the scientific literature from the γ-chloro- or γ-bromotiglic aldehyde by reaction with triphenylphosphine in toluene at about 110° C. (see Belgian Patent 656,433) or in diethyl ether [Helv. Chim. Acta 54, 1369 et seq. (1971)]. The production of the C₅-Wittig aldehyde bromide is also described in Finn. Chem. Lett. 1984, 102 et seq.

In addition to these known methods it has now been found that the reaction of γ-chlorotiglic aldehyde with triphenylphosphine in a solvent mixture of toluene and acetonitrile at about 80° C. gives the Wittig aldehyde salt in about 67% yield and in high purity (>99%) after a reaction period of about 5 hours. It has generally been established that the C₅-Wittig aldehyde bromide can be produced under milder reaction conditions than the corresponding chloride from the respective γ-halotiglic aldehyde and triphenylphosphine, namely already at about 40° C. in toluene or a mixture, preferably a 1:1 mixture, of toluene and acetonitrile in about 2 hours in contrast to over 5–8 hours at 80° C. in the mentioned solvent mixture. Other solvents such as, for example, ethyl acetate or cyclohexane (in each case used alone) can be used in the formation of the Wittig aldehyde salt, although the yields have been established to be somewhat lower.

It has been found to be practical to use the same solvent, e.g., toluene, in the working-up of the preceding chloro- or bromoalkoxylation and hydrolysis for the extraction which is required subsequently for the Wittig aldehyde salt formation. In this manner the Wittig salt can be advantageously produced using a "through process" II→III→I→VII, especially as the γ-chloro-or γ-bromotiglic aldehyde of formula I, which would otherwise require isolation and possibly also purification, is not particularly stable.

The use of the γ-chloro-or γ-bromotiglic aldehyde of formula I manufactured in accordance with the invention for the production of the respective C₅-Wittig aldehyde halide of formula VII represents a further aspect of the present invention.

The invention is illustrated by the following Examples.

A. Production of the 1-alkoxy-2-methyl-1,3-butadiene (compound of formula II)

EXAMPLE 1

1-Methoxy-2-methyl-1,3-butadiene [two steps a) and b)]

a) 1,1,3-Trimethoxy-2-methyl-butane 1035 g (11 mol) of acetaldehyde dimethyl acetal [purity according to gas chromatography (GC): 96.5%] and 3.4 g (3 ml, 24 mmol, 0.22 mol %) of boron trifluoride etherate were placed under argon in a 2 l two-necked round flask fitted with a magnetic stirrer, a thermometer and a dropping funnel. 530 g (7.35 mol) of methyl (1-propenyl) ether were added dropwise to the mixture within 2 hours at between 30° and 40° C. with occasional cooling (the reaction was exothermic). After completion of the addition the mixture was stirred for a further 30 minutes at 30° C., then cooled to room temperature. 3 ml of triethylamine were added thereto, the mixture was stirred for 15 minutes and suction filtered. The excess acetaldehyde dimethyl acetal was then distilled off on a Raschig column (50×3 cm) at normal pressure and the residue was fractionated on the same column. This gave at a pressure of 50 mbar a 1st fraction (b.p. 81.5°–83.5° C.) consisting of 742 g (60% yield) of 1,1,3-trimethoxy-2-methyl-butane (content according to GC: 96.4%) as a colourless liquid and a 2nd fraction (b.p. 83.5°–85° C.) consisting of 87.5 g (6.3% yield) of 1,1,3-trimethoxy-2-butane (content according to GC: 86%), likewise as a colourless liquid, i.e. a total yield of 66.3% of the desired product.

b) 1-Methoxy-2-methyl-1,3-butadiene (i) (1st variant)

An electrically heated steel tube (length 60 cm, diameter 2.7 cm, wall temperature 300° C.) was used as the reactor. The reaction tube was filled in the bottom with ceramic beads (10 cm high, diameter 6 mm). 100 ml of aluminium silicate-catalyst carrier having a specific surface of 15 m²/g were placed on top of the beads. The upper part of the reactor was filled with ceramic beads. 1,1,3-Trimethoxy-2-methyl-butane (60 ml/h.) and nitrogen (20 l/h) were introduced continuously into the reactor. The reaction products were condensed from the nitrogen stream in a condenser, cooled to 20° C., having a built-in fritz (mist separation), removed as a liquid and analyzed by gas chromatography. The conversion of the 1,1,3-trimethoxy-2-methyl-butane was 88%, the selectivity to 1-methoxy-2-methyl-1,3-butadiene was 90%. After separation of the methanol which had formed by extraction with alkaline water (pH >8) the organic phase was separated by rectification. 1-Methoxy-2-methyl-1,3-butadiene having a purity of about 99% was obtained.

(ii) (2nd variant)

The wall temperature of the reactor was adjusted to 250° C. All other conditions were the same as in Example b)(i). The conversion of 1,1,3-trimethoxy-2-methyl-butane was 41%, the selectivity to 1-methoxy-2-methyl-1,3-butadiene 90%.

(III) (3Rd. variant).

The wall temperature of the reactor was adjusted to 325° C. All other conditions were the same as in Example b)(i). The conversion of 1,1,3-trimethoxy-2-methyl-butane was 97.5%, the selectivity to 1-methoxy-2-methyl-1,3-butadiene 86%.

EXAMPLE 2

1-Ethoxy-2-methyl-1,3-butadiene [two steps a) and b)]

a) 1,1,3-Triethoxy-2-methyl-butane 900 g (7.4 mol) of acetaldehyde diethyl acetal (purity according to GC: 97%) and 0.85 g (0.75 ml, 6 mmol, 0.25 mol %) of boron trifluoride etherate were placed in a 2 l two-necked round flask fitted with a magnetic stirrer, a thermometer and a dropping funnel. 220 g (2.5 mol) of ethyl (1-propenyl) ether were added dropwise within about 30 minutes while cooling occasionally with ice at a temperature of about 35° C., but a maximum of 40° C. After completion of the addition the mixture was stirred at room temperature for a further 30 minutes. Then, 4 g of solid, powdered sodium carbonate were added thereto and the mixture was stirred at room temperature for 2.5 hours. Then the mixture was suction filtered and the excess acetaldehyde diethyl acetal was distilled off on a Raschig column, (30×2.5 cm) at 100 mbar. About 1 l of acetaldehyde diethyl acetal (content according to GC: 91%) was recovered in this manner at a boiling point of 40°–43° C. The residue was then fractionated on the same column at a pressure of 12–13 mbar. This gave 344.5 g (66.2% yield) of 1,1,3-triethoxy-2-methyl-butane as a water-clear liquid with a boiling point of 81°–84° C. and a content of 98.2% according to GC.

b) 1-Ethoxy-2-methyl-1,3-butadiene 1,1,3-Triethoxy-2-methyl-butane (60 ml/h) and nitrogen (20 l/h) were introduced into the reactor described in Example 1b) (same temperature, same catalyst). 90% of the 1,1,3-triethoxy-2-methyl-butane used was converted; the selectivity to 1-ethoxy-2-methyl-1,3-butadiene was about 90%. The reaction products were worked-up analogously to Example 1. 1-Ethoxy-2-methyl-1,3-butadiene was obtained with a purity of about 98%.

B. Manufacture of γ-halotiglic aldehyde (compound of formula I)

EXAMPLE 3

γ-Chlorotiglic aldehyde 10 g (82 mmol) of 1-ethoxy-2-methyl-1,3-butadiene were dissolved in 100 ml of ethanol in a 350 ml four-necked sulphonation flask. The solution was then cooled to 0° C. and treated dropwise within one hour with 90 g (160 mmol) of 13% aqueous sodium hypochlorite solution, which gave a white precipitate. Then the mixture was stirred at room temperature for about 30 minutes, poured into water and extracted four times with 100 ml, a total of 400 ml, of n-pentane. The entire pentane solution was stirred at room temperature for about one hour with 250 ml of 10% sulphuric acid. Subsequently, the aqueous phase was separated and the organic phase was washed in succession with 100 ml of sodium bicarbonate solution and 100 ml of sodium chloride solution, dried over anhydrous sodium sulphate and concentrated under reduced pressure. This gave 7 g of a yellow liquid which was chromatographed on 200 g of silica gel (0.04–0.063 mm) with cyclohexane/ethyl acetate (9:1). After bulb-tube distillation at about 100° C./15 mm Hg there were obtained 3.5 g (35% yield) of γ-chlorotiglic aldehyde as a colourless liquid with a purity of 97.1% according to GC.

Microanalysis: Calc. C 50.65% H 5.95% Cl 29.90% Found C 50.59% H 6.09% Cl 29.78%

$^1$H-NMR (250 MHz, CDCl$_3$): 1.83 ppm (s, 3H), 4.30 ppm (d, J≅8 Hz, 1H), 6.57 ppm (t, J~8 Hz, 1H), 9.49 ppm (s, 1H); IR (film): 1692, 1648; mass spectrum: 118 (M$^+$).

EXAMPLE 4

γ-Chlorotiglic aldehyde 22.7 g (0.2 mol) of 1-ethoxy-2-methyl-1,3-butadiene (purity according to GC: 99%) in 200 ml of methanol were placed under argon in a 500 ml four-necked sulphonation flask fitted with a mechanical stirrer, a dropping funnel and a thermometer. 140 g (0.24 mol, 1.2 eq.) of 13% aqueous sodium hypochlorite solution were added dropwise at about +5° C. while stirring within 15 minutes (because of an exothermic reaction). After completion of the addition the mixture was stirred at +5° C. for a further 15 minutes. Then a further 10 g (0.02 mol, 0.1 eq.) of 13% aqueous sodium hypochlorite solution were added dropwise at 0° C. The reaction mixture was then poured into 150 ml of water and extracted twice with 50 ml, a total of 100 ml, of n-pentane. The aqueous phase was then saturated with sodium chloride and again extracted with 50 ml of n-pentane.

The entire organic phase was washed with 25 ml of water and the two-phase solution was stirred at room temperature for about 30 minutes with 50 ml of 6N hydrochloric acid. The aqueous phase was then separated, saturated with sodium chloride and extracted with 50 ml of n-pentane. Thereafter, the combined organic phase was washed with 25 ml of saturated sodium bicarbonate solution, dried over anhydrous sodium sulphate, filtered and cautiously concentrated under reduced pressure. This gave 23 g of crude γ-chlorotiglic aldehyde as a pale yellow liquid having a purity of about 75% according to GC. The crude product was not investigated spectroscopically, but was reacted directly with triphenylphosphine according to Example 13.

EXAMPLE 5

γ-Chlorotiglic aldehyde 20.5 g (0.2 mol) of 1-methoxy-2-methyl-1,3-butadiene (purity according to GC: 96%) in 200 ml of methanol were reacted analogously to the procedure described in Example 4 at +5° C. with a total of 150 g (0.26 mol, 1.3 eq.) of 13% aqueous sodium hypochlorite solution. Subsequent analogous hydrolysis (100 ml of 3N hydrochloric acid/room temperature/about 30 minutes) and working-up gave 22 g of crude γ-chlorotiglic aldehyde as a yellowish oil having a purity of about 77% according to GC. Again, this crude product was not investigated spectroscopically, but was reacted directly with triphenylphosphine according to Example 14.

EXAMPLE 6

γ-Chlorotiglic aldehyde 22.7 g (0.2 mol) of 1-ethoxy-2-methyl-1,3-butadiene (purity according to GC: 99%) in 200 ml of methanol were reacted also analogously to the procedure described in Example 4 at 0° C. with 150 g (about 0.26 mol, 1.3 eq.) of 13% aqueous sodium hypochlorite solution for 30 minutes. Subsequent analogous working-up using 150 ml of n-pentane followed by acidic hydrolysis of the acetal with 50 ml of 6N hydrochloric acid at 0° C. over 30 minutes gave 26.8 g of crude γ-chlorotiglic aldehyde having a purity of about 73% according to GC as a dark yellow oil. The crude product was not investigated spectroscopically, but was converted directly into γ-acetoxy-tiglic aldehyde according to Example 15.

EXAMPLE 7

γ-Chlorotiglic aldehyde 10.1 g (0.1 mol) of 1-methoxy-2-methyl-1,3-butadiene were dissolved in 100 ml of methanol in a 200 ml four-necked sulphonation flask fitted with a magnetic stirrer, a dropping funnel and a thermometer. The solution was then cooled to −20° C. and treated dropwise within 30 minutes with 12.0 g (0.11 mol, 1.1 eq.) of tert.butyl hypochlorite. [For the production of this hypochlorite see Vogel's Textbook of Practical Organic Chemistry, 5th vol., Longman Group U.K. Ltd., 1989, page 422; Ed. B. S. Furniss et al.].

The clear solution obtained was poured into 200 ml of water and extracted three times with 50 ml, a total of 150 ml, of n-pentane. The pentane phases were combined and washed in succession with 25 ml of 5% sodium bisulphite solution and with 25 ml of water, then treated with 25 ml of 6N hydrochloric acid at 0° C. for about 30 minutes and stirred. 12.1 of crude γ-chlorotiglic aldehyde were obtained as a yellowish liquid after usual working-up. The crude product was not investigated spectroscopically, but was reacted directly with triphenylphosphine according to Example 16.

EXAMPLE 8

γ-Bromotiglic aldehyde

In a 200 ml four-necked sulphonation flask fitted with a magnetic stirrer and a thermometer 10.1 g (0.1 mol) of 1-methoxy-2-methyl-1,3-butadiene in 50 ml of methanol were treated portionwise with 15.6 g (0.11 mol) of N-bromoacetamide at about −7° C. to −12° C. while stirring within 30 minutes. The reaction mixture was then stirred at −10° C. for 30 minutes. The mixture was added to 100 ml of 2.5% sodium bicarbonate solution and then extracted three times with 50 ml, a total of 150 ml, of n-pentane.

The combined organic phases were washed with 25 ml of water, subsequently treated under argon with 30 ml of 6N hydrochloric acid and the two-phase mixture was stirred at 0° C. for one hour. The aqueous phase was then separated and extracted twice with 25 ml, a total of 50 ml, of n-pentane. Thereafter, the organic phases were combined and washed with 25 ml of saturated sodium bicarbonate solution, dried over anhydrous sodium sulphate, filtered and concentrated under reduced pressure. This gave 15.5 g of crude γ-bromotiglic aldehyde as a yellow liquid. The crude product was not investigated spectroscopically, but was reacted directly with triphenylphosphine according to Example 17.

EXAMPLE 9

γ-Chlorotiglic aldehyde 10.1 g (0.1 mol) of 1-methoxy-2-methyl-1,3-butadiene (purity according to GC: 97.5%) and 50 ml of methanol were placed under argon in a 200 ml four-necked sulphonation flask fitted with a magnetic stirrer and a thermometer. Then 12 g (98% pure, 0.06 mol) of 1,3-dichloro-5,5-dimethylhydantoin were added portionwise within about 30 minutes while stirring at about −10° C. to −5° C. After completion of the addition the mixture was stirred further at 0° C. for about one hour. The mixture, consisting of a colourless liquid and a beige coloured precipitate, was then poured into 200 ml of distilled water and extracted three times with 50 ml, a total of 150 ml, of n-pentane.

The combined organic phases were washed with 25 ml of water and the 2-phase solution was stirred with 25 ml of 6N hydrochloric acid at 0° C. for about one hour. The aqueous phase was then separated off and extracted twice with 25 ml, a total of 50 ml, of n-pentane. Finally, the entire organic phase was washed with 25 ml of saturated sodium bicarbonate solution, dried over anhydrous sodium sulphate, filtered and concentrated under reduced pressure. This gave 11.9 g of crude γ-chlorotiglic aldehyde as a yellowish liquid having a purity of about 77% according to GC. The crude product was not investigated spectroscopically, but was directly reacted with triphenylphosphine according to Example 18.

EXAMPLE 10

γ-Bromotiglic aldehyde 10.1 g (0.1 mol) of 1-methoxy-2-methyl-1,3-butadiene (purity according to GC: 97.5%) and 50 ml of methanol were placed in a 200 ml four-necked sulphonation flask fitted with a magnetic stirrer and a thermometer. 16 g (97% pure, 0.054 mol) of 1,3-dibromo-5,5-dimethyl-hydantoin were then added portionwise within about 30 minutes while stirring at about −15° C. to −10° C. After completion of the addition the mixture was stirred at −10° C. for about a further 30 minutes. The mixture, consisting of a yellowish liquid and a white precipitate, was then poured into 100 ml of saturated sodium bicarbonate solution and extracted three times with 50 ml, a total of 150 ml, of n-pentane.

The combined organic phases were washed with 25 ml of distilled water and the two-phase solution was stirred with 30 ml of 6N hydrochloric acid at 0° C. for about one hour. The aqueous phase was then separated off and extracted twice with 25 ml, a total of 50 ml, of n-pentane. Finally, the entire organic phase was washed with 25 ml of saturated sodium bicarbonate solution, dried over anhydrous sodium sulphate, filtered and concentrated under reduced pressure. This gave 16.6 g of crude γ-chlorotiglic aldehyde as a yellowish liquid having a purity of about 95% according to GC. The crude product was not investigated spectroscopically, but was reacted directly with triphenylphosphine according to Example 19.

EXAMPLE 11

γ-Bromotiglic aldehyde (and its conversion into the $C_5$-Wittig aldehyde bromide of formula VII using a through process)

11.7 g (0.1 mol) of 1-ethoxy-2-methyl-1,3-butadiene (purity according to GC: 96%) in 100 ml of methanol were placed in a 350 ml four-necked sulphonation flask fitted with a mechanical stirrer, a dropping funnel and a thermometer. 65 g (0.125 mol) of 23% sodium hypobromite solution, freshly prepared by dissolving 11 g (0.28 mol) of sodium hydroxide platelets in 35 ml of water and adding about 6.6 ml (20.5 g, 0.13 mol) of bromine dropwise at 0° C. in about 30 minutes (pH about 12.7–12.9), were added dropwise at −10° C. while stirring vigorously, and then the mixture was stirred at −10° C. for a further 15 minutes. Then the reaction mixture was poured into 50 ml toluene and washed with 100 ml of water. The milky aqeuous phase was again extracted with 50 ml of toluene. The entire organic phase was washed with 25 ml of water and the resulting two-phase solution was subsequently stirred magnetically under argon with 30 ml of 6N aqueous hydrochloric acid at 0° C. for 45 minutes. The aqueous phase was separated and again extracted with 25 ml of toluene. The combined toluene phases were then washed with 25 ml of saturated sodium bicarbonate solution, dried over anhydrous sodium sulphate, filtered and introduced under argon into a 350 ml four-necked sulphonation flask fitted with a mechanical stirrer and a thermometer.

23.5 g (0.09 mol, 0.9 eq.) of triphenylphosphine were added to the solution while stirring and the mixture was stirred at 40° C. for about 16 hours (crystallization began even after a few minutes at room temperature). The resulting beige suspension was then cooled to 0° C. within 15 minutes, suction filtered and washed three times with 25 ml, a total of 75 ml, of toluene at 0° C. After drying there were obtained 30.0 g (69.8%) of $C_5$-Wittig aldehyde bromide as a white crystalline powder with m.p. 256°–257° C. and a content of 98.95% according to HPLC.

EXAMPLE 12

γ-Bromotiglic aldehyde (and its conversion into γ-acetoxy-tiglic aldehyde using a through process)

11.7 g (0.1 mol) of 1-ethoxy-2-methyl-1,3-butadiene in 100 methanol were reacted analogously to the procedure described in the Example 11 at −10° C. with 70 g (about 0.135 mol) of 23% sodium hypobromite solution. Analogous three-fold extraction with 50 ml, a total of 150 ml, of toluene, hydrolysis with 30 ml of 6N hydrochloric acid at 0° C. as well as extraction of the hydrochloric acid phase with an additional 50 ml of toluene gave a solution of γ-bromotiglic aldehyde in about 200 ml of toluene.

After drying over anhydrous sodium sulphate this solution was stirred under argon with 15 g (0.15 mol) of potassium acetate and 1 g (4.8 mol, 5 mol%) of tetraethylammonium bromide at 80° C. for 2½ hours in a 350 ml sulphonation flask fitted with a mechanical stirrer, a condenser and a thermometer. The mixture was then cooled to +10° C., filtered and carefully concentrated under reduced pressure. This gave 18.6 g of crude γ-acetoxy-tiglic aldehyde as a yellowish liquid. Distillation (Vigreux) at 20 mbar gave at a boiling point of 101°–103° C. 8.4 g (56.4% yield) of γ-acetoxy-tiglic aldehyde as a yellow liqiud having a content of 95.4% according to GC.

C. Conversion of the γ-halotiglic aldehyde of formula I into the $C_5$-Wittig aldehyde halide or γ-acetoxy-tiglic aldehyde.

EXAMPLE 13

$C_5$-Wittig aldehyde chloride

The crude product of Example 4 was dissolved in 80 ml of acetonitrile and 80 ml of toluene in a 500 ml round flask fitted with a magnetic stirrer and a condenser. The solution was then treated with 57 g (0.22 mol) of triphenylphosphine and refluxed at about 85° C. for about 5 hours. The resulting suspension (a yellow-orange solution with a beige precipitate) was cooled to about +3° C., suction filtered and washed twice with 50 ml, a total of 100 ml, of toluene. The filter material was then dried for 3 hours at 50° C. under a water-jet vacuum. This gave 51.0 g (66.6% yield based on 1-ethoxy-2-methyl-1,3-butadiene) of $C_5$-Wittig aldehyde chloride as a light beige, crystalline powder with a melting point of 247°–248° C. and a content of 99.4% according to HPLC.

Microanalysis: Calc. C 72.53% H 5.82% Cl 9.31% Found C 72.23% H, 5.75% Cl 9.40%

EXAMPLE 14

$C_5$-Wittig aldehyde chloride

The crude product of Example 5 was reacted with 53 g (0.2 mol) of triphenylphosphine in 80 ml of acetonitrile and 80 ml of toluene analogously to the procedure described in Example 13. This gave 51.0 g (66.5% yield based on 1-methoxy-2-methyl-1,3-butadiene) of $C_5$-Wittig aldehyde chloride as a white powder with a melting point of 247°–248° C. and a content of 99.2% according to HPLC.

EXAMPLE 15

γ-Acetoxy-tiglic aldehyde

The crude product of Example of 6 was taken up in 200 ml of toluene in a four-necked sulphonation flask fitted with a mechanical stirrer and treated with 25 g (0.25 mol, 1.25 eq.) of potassium acetate and 600 mg (2.8 mmol, 1.5 mol%) of tetraethylammonium bromide. The mixture was boiled at reflux temperature for 1½ hours while stirring. Then the suspension was cooled to 5° C., filtered and carefully evaporated under reduced pressure. This gave 18.8 g of crude -acetoxy-tiglic aldehyde as an orange-brown oil. Distillation on a (20 cm/Ø14.5) Vigreux column at 11 mbar gave as the main fraction (b.p. 90°–92.5° C.) 14.9 g (46% yield based on 1-ethoxy-2-methyl-1,3-butadiene) of γ-acetoxy-tiglic aldehyde as a yellow oil having a content of 87.8% according to GC.

EXAMPLE 16

$C_5$-Wittig aldehyde chloride

Analogously to the procedure described in Example 13, the crude product of Example 7 was reacted with 26.2 g (0.1 mol) of triphenylphosphine in 40 ml acetonitrile and 40 ml of toluene at reflux temperature for 18 hours. This gave 28.0 g (73.4% yield based on 1-methoxy-2-methyl-1,3-butadiene) of $C_5$-Wittig aldehyde bromide as a snow-white, crystalline powder with a melting point of 254°–255° C. and a content of 99.7% according to HPLC.

EXAMPLE 17

$C_5$-Wittig aldehyde bromide

Analogously to the procedure described in Example 13, the crude product of Example 8 was reacted with 27.5 g (0.105 mol) of triphenylphosphine in 50 ml of acetonitrile and 50 ml of acetone at 40° C. for 2 hours. This gave 34.1 g (80.1% yield based on 1-methoxy-2-methyl-1,3-butadiene) of $C_5$-Wittig aldehyde bromide as a snow-white, crystalline powder with a melting point of 254°–255° C. and a content of 98.7% according to HPLC.

EXAMPLE 18

$C_5$-Wittig aldehyde chloride

Analogously to the procedure described in Example 13, the crude product of Example 9 was reacted with 26.2 g (0.1 mol) of triphenylphosphine in 40 ml of acetonitrile and 40 ml of toluene at reflux temperature for 16 hours. This gave 27.6 g (72.5% yield based on 1-methoxy-2-methyl-1,3-butadiene) of $C_5$-Wittig aldehyde chloride as a white powder with a melting point of 247°–248° C.

EXAMPLE 19
$C_5$-Wittig aldehyde bromide

Analogously to the procedure described in Example 13, the crude product of Example 10 was reacted with 27.5 g (about 1.05 eq.) of triphenylphosphine in 50 ml of acetonitrile and 50 ml of toluene at 40° C. for 2 hours and subsequently at 0° C. for a further 45 minutes. This gave 36.4 g (85.6% yield based on 1-methoxy-2-methyl-1,3-butadiene) of $C_5$-Wittig aldehyde bromide as a snow-white powder with a melting point of 255°–256° C. (decomposition).

We claim:

1. A process for making a γ-chloro- or γ-bromotiglic aldehyde of the formula:

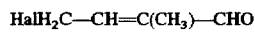
$$HalH_2C-CH=C(CH_3)-CHO \qquad I$$

wherein Hal is chlorine or bromine,
which process comprises:
1) haloalkoxylating a 1-alkoxy-2-methyl-1,3-butadiene of the formula:

$$H_2C=CH-C(CH_3)=CH-OR^1 \qquad II$$

wherein $R^1$ is $C_{1-4}$-alkyl,
by reacting the 1-alkoxy-2-methyl-1,3-butadiene with a halogenating agent and an alcohol of the formula $R^2OH$, wherein the halogenating agent is selected from the group consisting of an alkali metal hypochlorite, an alkali metal hypobromite, an alkaline earth metal hypochlorite, an alkaline earth metal hypobromite, tert.butyl hypochlorite, N-bromoacetamide, 1,3-dichloro-5,5-dimethyl-hydantoin and 1,3-dibromo-5,5-dimethyl-hydantoin, and $R^2$ is $C_{1-4}$-alkyl, to obtain a γ-halotiglic aldehyde dialkyl acetal of the formula:

$$HalH_2C-CH=C(CH_3)-CH(OR^1)(OR^2) \qquad III$$

wherein Hal, $R^1$ and $R^2$ are as above, and
2) hydrolyzing the γ-halotiglic aldehyde dialkyl acetal under hydrolysis conditions, whereby the γ-chloro- or γ-bromotiglic aldehyde is produced.

2. The process of claim 1 the wherein the halogenating agent is an alkali metal or alkaline earth metal hypohalite.

3. The process of claim 2 wherein the halogenating agent is selected from the group consisting of sodium hypochlorite, potassium hypochlorite, sodium hypobromite and potassium hypobromite.

4. The process of claim 3 wherein $R^1$ and $R^2$ are independently methyl or ethyl.

5. The process of claim 4 wherein the amount of the halogenating agent is in a range from about 1.1 to about 1.4 equivalents per equivalent of 1-alkoxy-2-methyl-1,3-butadiene of formula II.

6. The process of claim 5 wherein the amount of the alcohol $R^2OH$ is in a range from about ten fold to about thirty fold stoichiometric excess.

7. The process of claims 6 wherein the haloalkoxylation is carried out at a temperature in a range from about −20° C. to about room temperature.

8. The process of claim 7 wherein the haloalkoxylation is carried out at a temperature in a range from about −20° C. to about +5° C.

* * * * *